(12) United States Patent
Dahlström

(10) Patent No.: US 7,345,061 B2
(45) Date of Patent: Mar. 18, 2008

(54) ALKYLAMMONIUM SALTS OF OMEPRAZOLE AND ESOMEPRAZOLE

(75) Inventor: Mikael Dahlström, Mölndal (SE)

(73) Assignee: AstraZeneca AB, Södertälje (SE)

( * ) Notice: Subject to any disclaimer, the term of this patent is extended or adjusted under 35 U.S.C. 154(b) by 91 days.

(21) Appl. No.: 10/506,345

(22) PCT Filed: Mar. 4, 2003

(86) PCT No.: PCT/SE03/00378

§ 371 (c)(1),
(2), (4) Date: Sep. 1, 2004

(87) PCT Pub. No.: WO03/074514

PCT Pub. Date: Sep. 12, 2003

(65) Prior Publication Data

US 2005/0182099 A1    Aug. 18, 2005

(51) Int. Cl.
*A61K 31/4439*    (2006.01)
*C07D 401/12*    (2006.01)
(52) U.S. Cl. .................................. 514/338; 546/273.7
(58) Field of Classification Search ............. 546/273.7; 514/338
See application file for complete search history.

(56) References Cited

FOREIGN PATENT DOCUMENTS

| | | |
|---|---|---|
| EP | 0005129 A1 | 10/1979 |
| EP | 0124495 A2 | 11/1984 |
| EP | 0247983 A2 | 2/1987 |
| WO | WO-94/27988 | 12/1994 |
| WO | WO-96/01623 | 1/1996 |
| WO | WO-96/02535 | 2/1996 |
| WO | WO-97/41114 | 11/1997 |
| WO | WO-98/54171 | 12/1998 |

*Primary Examiner*—Patricia L. Morris
(74) *Attorney, Agent, or Firm*—White & Case LLP

(57) ABSTRACT

The present invention relates to new salts of omeprazole and esomeprazole respectively, i.e. salts of 5-methoxy-2-[[(4-methoxy-3,5-dimethyl-2-pyridinyl)-methyl]sulfinyl]-1H-benzimidazole and the (S)-enantiomer thereof. More specifically, the present invention relates to alkylammonium salts of the compounds, formed by a reaction of omeprazole and esomeprazole respectively and an alkylamine with formula $NR_1R_2R_3$, wherein $R_1$ is a linear, branched, or cyclic $C_1$-$C_{12}$-alkyl group, and $R_2$ and $R_3$ are hydrogen. The present invention also relates to a process for preparing crystalline salts, a pharmaceutical preparation, and a method for treatment of gastric related disorders by administering the compound of the invention.

22 Claims, 2 Drawing Sheets

ALKYLAMMONIUM SALTS OF OMEPRAZOLE AND ESOMEPRAZOLE

FIELD OF THE INVENTION

The present invention relates to novel salts of 5-methoxy-2-[[(4-methoxy-3,5-dimethyl-2-pyridinyl)-methyl]sulfinyl]-1H-benzimidazole or salts of the single enantiomers thereof in a pure and isolated form. Specifically, it relates to alkylammonium salts of the compounds, more specifically primary alkylammonium salts of the compounds. The present invention also relates to processes for preparing certain alkylammonium salts of omeprazole and esomeprazole in a pure and isolated form and pharmaceutical compositions containing them.

BACKGROUND OF THE INVENTION AND PRIOR ART

The compound 5-methoxy-2-[[(4-methoxy-3,5-dimethyl-2-pyridinyl)methyl]sulfinyl]-1H-benzimidazole, having the generic name omeprazole, and therapeutically acceptable salts thereof, are described in EP 0 005 129.

Omeprazole is a sulfoxide and a chiral compound, wherein the sulphur atom being the stereogenic center. Thus, omeprazole is a racemic mixture of its two single enantiomers, the R- and S-enantiomer of omeprazole, herein referred to as R-omeprazole and S-omeprazole, the latter have the generic name esomeprazole. The absolute configuration of the enantiomers of omeprazole has been determined by an X-ray study of an N-alkylated derivate of the R-enantiomer.

Omeprazole and esomeprazole are proton pump inhibitors, and are useful as antiulcer agents. In a more general sense, omeprazole and esomeprazole may be used for prevention and treatment of gastric acid related diseases in mammals and especially in man.

Specific alkaline salts of omeprazole are disclosed in EP 0 124 495. Herein, quaternary ammonium salts and guanidine salts of omeprazole are disclosed. Document WO 97/41114 discloses processes for preparing magnesium salt of benzimidazoles, including magnesium salt of omeprazole. However, no salts of omeprazole prepared from primary amines are mentioned in these documents.

Certain salts of the single enantiomers of omeprazole and their preparation are disclosed in WO 94/27988, for instance, quaternary ammonium salts of esomeprazole are mentioned. However, no salts employing primary, secondary or tertiary amines are disclosed or suggested. The described salts of esomeprazole have improved pharmacokinetic and metabolic properties, which will give an improved therapeutic profile such as a lower degree of interindividual variation. WO 96/02535 and WO 98/54171 disclose preferred processes for preparing esomeprazole and salts thereof.

In the formulation of drug compositions, it is important for the active pharmaceutical ingredient to be in a form in which it can be conveniently handled and processed. This is of importance, not only from the point of view of obtaining a commercially viable manufacturing process, but also from the point of view of subsequent manufacture of pharmaceutical formulations (e.g. oral dosage forms such as tablets) comprising the active pharmaceutical ingredient.

Further, in the manufacture of oral pharmaceutical compositions, it is important that a reliable, reproducible and constant plasma concentration profile of the active pharmaceutical ingredient is provided following administration to a patient.

Chemical stability, solid state stability, and "shelf life" of the active pharmaceutical ingredient are important properties for a pharmaceutical active compound. The active pharmaceutical ingredient, and compositions containing it, should be capable of being effectively stored over appreciable periods of time, without exhibiting a significant change in the physico-chemical characteristics of the active pharmaceutical ingredient, e.g. its chemical composition, density, hygroscopicity and solubility. Thus, in the manufacture of commercially viable and pharmaceutically acceptable drug compositions, it is important, wherever possible, to provide the active pharmaceutical ingredient in a substantially crystalline and stable form.

DRAWINGS

DESCRIPTION OF THE INVENTION

Figure 1:
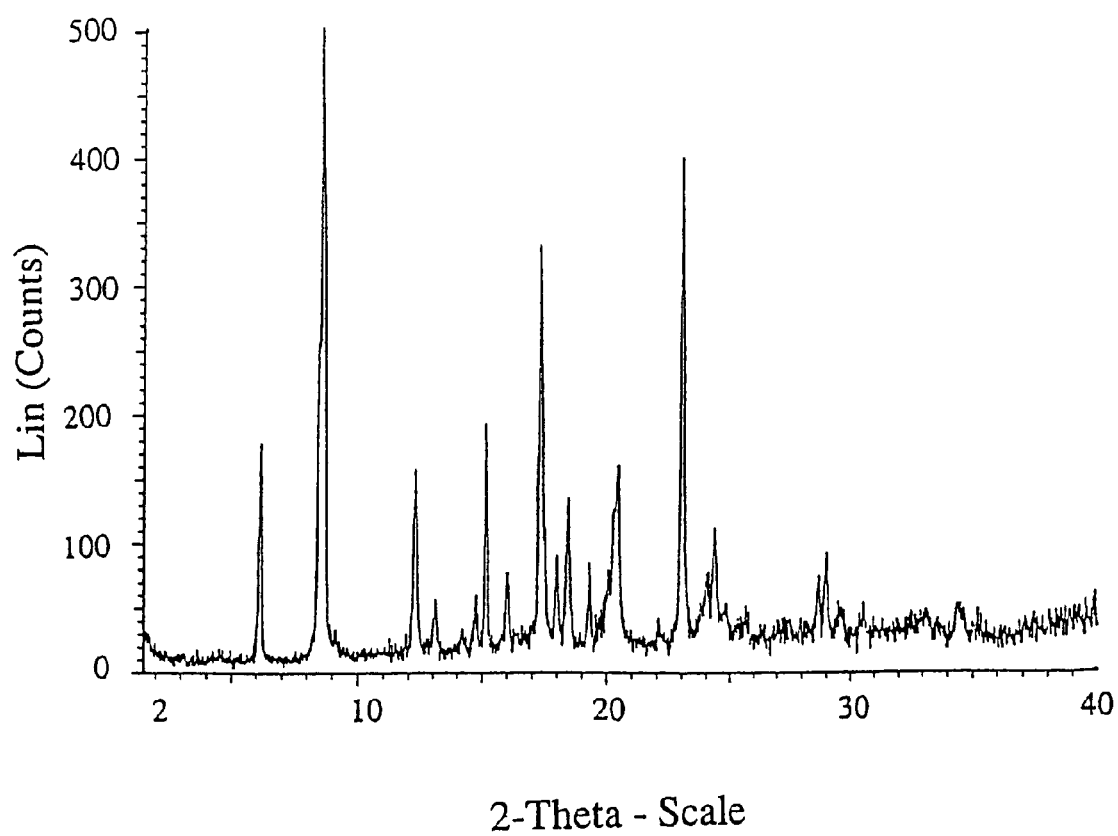
FIG. 1 is an X-ray powder diffractogram of the tert-butylammoniumsalt of omeprazole.

The present invention refers to new alkylammoniumsalts having the following formula (I) including compounds Ia, Ib and Ic:

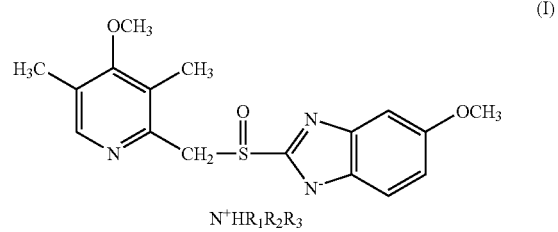

(I)

Formula Ia: alkylammoniumsalts of racemic omeprazole
Formula Ib: alkylammoniumsalts of the (S)-enantiomer of omeprazole
Formula Ic: alkylammoniumsalts of the (R)-enantiomer of omeprazole wherein $R_1$ is selected from linear, branched or cyclic $C_1$-$C_{12}$-alkyl group; $R_2$ is hydrogen; a linear, branched or cyclic $C_1$-$C_{12}$-alkyl group; and, $R_3$ is hydrogen; a linear, branched or cyclic $C_1$-$C_{12}$-alkyl group.

Further, the compound of the invention is alkylammoniumsalt of Formula Ia and Ib wherein the substituents $R_1$, $R_2$ and $R_3$ are defined as follows: $R_1$ is a linear or branched $C_1$-$C_6$ alkyl group; $R_2$ is hydrogen; a linear or branched $C_1$-$C_6$ alkyl group; $R_3$ is hydrogen; a linear or branched $C_1$-$C_6$ alkyl group.

In a further aspect of the invention, the $NHR_1R_2R_3^+$ salt of omeurazole or esomeurazole has a pKa value being equal to or above 10. More preferred is a pKa value of equal to or above 10.5.

The compounds of the invention may be prepared in the form of solvates, hydrates, and anhydrates.

In a further aspect, the present invention provides processes for the preparation of alkylammonium salts of omeprazole and of esomeprazole. It has surprisingly been found that alkylammonium salts of omeprazole and alkylammonium salts of the R- and S-enantiomers thereof may be obtained in a well-defined crystalline state. More specifically, the compounds tert-butylammoniumsalt of omeprazole and tert-butylammoniumsalt of esomeprazole according to the present invention are characterized by being highly crystalline with a well-defined structure.

The chemical name 5-methoxy-2-[[(4-methoxy-3,5-dimethyl-2-pyridinyl)-methyl]sulfinyl]-1H-benzimidazole tert-butyl ammonium salt as well as the chemical name S-5-methoxy-2-[[(4-methoxy-3,5-dimethyl-2-pyridinyl)methyl] sulfinyl]-1H-benzimidazole tert-butyl ammonium salt does not necessarily mean that the methoxy group of the two benzimidazole moieties is in the 5-position but may as well be in the 6-position, or there may be mixtures of the two.

One embodiment of the invention is a compound of Formula Ia and Ib wherein, $R_1$ is selected from linear, branched $C_1$-$C_{12}$-alkyl group, or cyclic $C_3$-$C_{12}$- alkyl group wherein the linear or branched alkyl group may be substituted or interrupted with a cyclic $C_3$-$C_6$-alkyl or cyclic $C_3$-$C_6$ alkylene group or with a phenyl or phenylene group; and wherein the cyclic alkyl or cyclic alkylene group or the phenyl or phenylene group is further substituted by 0, 1, 2, or 3 methyl groups; and $R_2$ and $R_3$ are hydrogen.

Another embodiment of the invention is a compound of Formula Ia and Ib wherein $R_2$ and $R_3$ are hydrogen, and $R_1$ has any of the meanings defined in paragraphs a) to g) hereinafter:

a) $R_1$ is a linear or branched $C_2$-$C_{11}$-alkyl group, or cyclic $C_3$-$C_{11}$-alkyl group wherein the linear or branched alkyl group may be substituted or interrupted with a cyclic $C_3$-$C_6$-alkyl or cyclic $C_3$-$C_6$ alkylene group or with a phenyl or phenylene group; and wherein the cyclic alkyl or cyclic alkylene group or the phenyl or phenylene group is further substituted by 0, 1, 2, or 3 methyl groups;

b) $R_1$ is a linear, branched or cyclic $C_3$-$C_{10}$-alkyl group, wherein the linear or branched alkyl group may be substituted or interrupted with a cyclic $C_3$-$C_6$-alkyl or cyclic $C_3$-$C_6$ alkylene group or with a phenyl or phenylene group; and wherein the cyclic alkyl or cyclic alkylene group or the phenyl or phenylene group is further substituted by 0, 1, 2 or 3 methyl groups;

c) $R_1$ is selected from linear, branched or cyclic $C_4$-$C_9$-alkyl group, wherein the linear or branched alkyl group may be substituted or interrupted with a cyclic $C_3$-$C_6$-alkyl or cyclic $C_3$-$C_6$ alkylene group or with a phenyl or phenylene group; and wherein the cyclic alkyl or cyclic alkylene group or the phenyl or phenylene group is further substituted by 0, 1, 2 or 3 methyl groups;

d) $R_1$ is selected from linear, branched or cyclic $C_4$-$C_8$- alkyl group wherein the linear or branched alkyl group may be substituted or interrupted with a cyclic $C_3$-$C_6$- alkyl or cyclic $C_3$-$C_6$ alkylene group or with a phenyl or phenylene group; and wherein the cyclic alkyl or cyclic alkylene group or the phenyl or phenylene group is further substituted by 0, 1, 2 or 3 methyl groups;

e) $R_1$ is selected from linear, branched or cyclic $C_4$-$C_7$- alkyl group wherein the linear or branched alkyl group may be substituted or interrupted with a cyclic $C_3$-$C_6$- alkyl or cyclic $C_1$-$C_6$ alkylene group or with a phenyl or phenylene group; and wherein the cyclic alkyl or cyclic alkylene group or the phenyl or phenylene group is further substituted by 0, 1, 2 or 3 methyl groups;

f) $R_1$ is selected from linear, branched or cyclic $C_1$-$C_6$- alkyl group wherein the linear or branched alkyl group may be substituted or interrupted with a cyclic $C_3$-$C_5$- alkyl or cyclic $C_3$-$C_5$ alkylene group or with a phenyl or phenylene group; and wherein the cyclic alkyl or cyclic alkylene group or the phenyl or phenylene group is further substituted by 0, 1, 2 or 3 methyl groups;

g) $R_1$ is selected from linear, branched or cyclic $C_4$-alkyl group wherein the linear or branched alkyl group may be substituted or interrupted with a cyclic $C_3$-alkyl or cyclic $C_3$-alkylene group; and wherein the cyclic alkyl or cyclic alkylene group is further substituted by 0, 1, 2 or 3 methyl groups.

As used herein, the term "linear $C_1$-$C_{12}$-alkyl group" is a linear alkyl group having 1 to 12 carbon atoms. Examples of said group includes, but is not limited to, methyl, ethyl, propyl, butyl, pentyl, hexyl, heptyl, octyl, nonyl, dekanyl.

The term "branched $C_1$-$C_{12}$-alkyl group" is a branched alkyl group having 1 to 12 carbon atoms. Examples of said group includes, but is not limited to, iso-propyl, iso-butyl, sec-butyl, tert-butyl, sec-pentyl, iso-pentyl, neo-pentyl.

The term "cyclic $C_3$-$C_{12}$-alkyl group" is a cyclic alkyl group having 3 to 12 carbon atoms. The cyclic group may be a mono, di or polycyclic-group, and it may also be substituted with 0, 1, 2, or 3 methyl groups. Examples of said group includes, but is not limited to, cyclopropyl, cyclobutyl, cyclopentyl, cyclohexyl.

In a further aspect of the invention, the $NHR_1R_2R_3^+$ has a pKa value being equal or more than 10. More preferred is a value of more than 10.5.

Another embodiment of the invention is the tert-butylammonium salt (i.e. 2-methyl-2-propan ammonium salt) of esomeprazole. This compound of the invention is characterized in providing an X-ray powder diffraction pattern, as in FIG. 2, exhibiting substantially the following d-values and intensities:

| d-value (Å) | Relative intensity |
|---|---|
| 14.5 | vs |
| 10.0 | vs |
| 7.3 | vs |
| 6.8 | m |
| 6.6 | s |
| 6.1 | m |
| 5.9 | s |
| 5.8 | vs |
| 5.5 | v |
| 5.4 | m |
| 5.3 | m |
| 5.1 | vs |
| 5.0 | s |
| 4.92 | vs |
| 4.87 | vs |
| 4.80 | vs |
| 4.56 | s |
| 4.49 | m |
| 4.39 | s |
| 4.30 | vs |
| 4.03 | s |
| 3.88 | vs |
| 3.67 | vs |
| 3.67 | s |
| 3.62 | s |
| 3.57 | m |
| 3.41 | m |
| 3.19 | m |
| 3.14 | s |
| 3.14 | s |
| 3.10 | m |
| 2.98 | m |
| 2.91 | m |
| 2.85 | m |
| 2.81 | m |
| 2.78 | m |

-continued

| d-value (Å) | Relative intensity |
|---|---|
| 2.63 | s |
| 2.34 | m |
| 2.32 | m |

Another embodiment of the invention is the tert-butylammonium salt of omeprazole. This compound of the invention is characterized in providing an X-ray powder diffraction pattern, as in FIG. 1, exhibiting substantially the following d-values and intensities:

| d-value (Å) | Relative intensity |
|---|---|
| 14.5 | vs |
| 10.4 | vs |
| 10.3 | vs |
| 7.2 | vs |
| 6.8 | m |
| 6.2 | m |
| 6.0 | m |
| 5.8 | vs |
| 5.5 | s |
| 5.1 | vs |
| 5.1 | s |
| 4.93 | s |
| 4.81 | s |
| 4.60 | s |
| 4.42 | s |
| 4.37 | s |
| 4.37 | s |
| 4.34 | vs |
| 4.02 | m |
| 3.86 | vs |
| 3.70 | s |
| 3.65 | s |
| 3.59 | m |
| 3.11 | s |
| 3.08 | s |
| 3.02 | m |
| 2.92 | m |
| 2.60 | m |

The peaks, identified with d-values calculated from the Bragg formula and intensities, have been extracted from the diffractogram of tert-butylammonium salt of esomeprazole and omeprazole, respectively. The relative intensities are less reliable and instead of numerical values, the following definitions are used;

| % relative Intensity* | Definition |
|---|---|
| 25-100 | vs (very strong) |
| 10-25 | s (strong) |
| 3-10 | m (medium) |
| 1-3 | w (weak) |

*the relative intensities are derived from the diffractograms measured with variable slits. The XRPD distance values may vary in the range of ±2 on the last decimal place.

X-ray powder diffraction (XRPD) analysis was performed on samples of tert-butylammonium salt of omeprazole and on samples of tert-butylammoniumsalt of esomeprazole, according to standard methods, for example, those described in Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray analyses were performed using a Siemens D5000 diffractometer.

The compounds of the invention are characterized by the positions and intensities of the peaks in the X-ray powder diffractogram, as well as by the unit cell parameters. Furthermore, the compounds of the invention could be characterized by $H^1$-NMR, IR, FTIR and Raman spectroscopy.

In a further aspect, the present invention provides processes for the preparation of alkylammoniumsalts of omeprazole and of esomeprazole. Suitable processes for the salt formation are temperature induced crystallisation, fast crystallisation at elevated temperature, slow crystallisation at room temperature, thermal recrystallisation, and crystallisation by evaporation.

In a further aspect, the present invention provides processes for the preparation of alkylammonium salts of omeprazole and of esomeprazole, which comprises the following steps: omeprazole or esomeprazole is either dissolved or formed in situ in a suitable solvent, such as acetonitril or tert-butyl methyl ether. The alkylamine is added during stirring. A precipitate of the salt compound is formed and the precipitate is separated by filtration. The obtained compound is washed with a solvent and the obtained crystals are dried.

A further aspect of the invention is that a crystallisation of the product provides that the salt can be quickly and easily filtered off and dried, and thus decreasing the time of processing. The addition of an alkylamine can easily and conveniently be performed on a large scale since alkylamines preferred for performing the present invention are liquids having low viscosity. Furthermore, during the process, any excess of the alkylamine is easily removed by drying since use of alkylamines having low boiling point is preferred. Therefore, the alkylamine used in the reaction can be added in excess, which is of considerable advantage in full-scale production.

Still a further aspect of the invention is that the novel compounds may be of interest as intermediates in the synthesis of other compounds such as magnesium salts of omeprazole and of esomeprazole, which are the pharmaceutically active components in products with the tradenames Losec® MUPS® and Nexium®. During the synthesis of the active component for Nexium® i.e. the magnesium salt of esomeprazole, a titanium catalyst may be used in the oxidation step prior to the salt formation steps. The synthesis usually proceeds with the formation of monovalent salt of esomeprazole by adding a monovalent hydroxide or alkoxide. This monovalent salt of esomeprazole, such as sodium or potassium salts, is thereafter converted to the magnesium salt. Insoluble inorganic titanium salts, such as titanium oxid, are being formed when strong bases such as sodium or potassium alkoxides are being added to a solution of titanium catalysts. Using an alkylamine as a salt forming agent rather than using a sodium- or potassium-containing base avoids the risk of inorganic titanium salts being co-precipitated with the desired salt. Even, if the titanium-catalyst may react with the alkylamine, a soluble complex of the alkylamine and titanium may be formed, which may stay in the solution while filtering off the desired alkylammonium salt of the benzimidazole compound.

As synthetic intermediate salts, alkylammonium salts of omeprazole and esomeprazole obtainable from easily removable amines are desired. In previous known processes for producing salts of esomeprazole (described in WO 96/02535 and WO 98/54171) an exchange of the metal ion is performed. For example, in the process for producing magnesium salt of esomeprazole, an intermediate salt consisting of the potassium salt of esomeprazole is formed which may result in residues of potassium ions as impurity ions in the desired, magnesium salt of esomeprazole.

By preparing and using the alkylammoniumsalts as intermediate salts, undesired components are avoided in the final product, i.e. the magnesium salt, as alkylamine is being released during the addition of a magnesium source. Liberated alkylamine can then be removed either by drying the magnesium salt in vacuum or by washing the magnesium salt.

The compounds of the invention are surprisingly easily soluble in water. This property is of great advantage, for instance when an i.v.-formulation should be prepared. Solutions containing the dissolved and ionised alkylammonium salt of omeprazole or alkylammonium salt of esomeprazole have a lower pH than corresponding solutions made from the previously known alkali-salts of omeprazole and of esomeprazole. A less basic solution is advantageous for i.v. administration.

The examplified tert-butylammonium salts of omeprazole and esomeprazole, respectively, are in crystalline forms. They exhibit advantageous properties, such as convenient handling as well as chemical and solid-state stability. The products obtained according to the present invention are well-defined crystalline products. Such crystalline products give an easily processability during the manufacture of suitable dosage forms. A crystalline product is easy to handle during milling, filtering and tableting. The procedures have high reproducibility. Also, the stability is improved when a well-defined crystalline form of the compound is obtained. These properties are of great value considering dosage forms such as e.g. tablets.

The compounds of the invention are effective as a gastric acid secretion inhibitor, and are useful as an antiulcer agent. In a more general sense, they can be used for prevention and treatment of gastric-acid related conditions in mammals and especially in man, including e.g. reflux esophagitis, gastritis, duodenitis gastric ulcer and duodenal ulcer. Furthermore, they may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. The compounds of the invention may also be used in patients in intensive care situations, in patients with acute upper gastrointestinal bleeding, pre- and postoperatively to prevent aspiration of gastric acid, to prevent and treat stress ulceration and asthma, and for improvement of sleep. Further, the compounds of the invention may be useful in the treatment of psoriasis as well as in the treatment of Helicobacter infections and diseases related to these. The compounds of the invention may also be used for treatment of inflammatory conditions in mammals, including man.

For the avoidance of doubt, by "treatment" is meant to include the therapeutic treatment as well as the prophylaxis, of a condition.

Any suitable route of administration may be employed for providing the patient with an effective dosage of the alkyl ammonium salt of omeprazole or esomeprazole, according to the invention. For example, peroral or parenteral formulations and the like may be employed. Dosage forms include capsules, tablets, dispersions, suspensions and the like.

It is further provided a pharmaceutical composition comprising the compounds according to the invention, as active ingredient, in association with a pharmaceutically acceptable carrier, diluent or excipient and optionally other therapeutic ingredients. Compositions comprising other therapeutic ingredients are especially of interest in the treatment of Helicobacter infections. The invention also provides the use of the compounds in the manufacture of a medicament for use in the treatment of a gastric-acid related condition and a method of treating a gastric-acid related condition which method comprises administering to a subject suffering from said condition a therapeutically effective amount of the compounds according to the invention.

The composition of the invention includes compositions suitable for peroral or parenteral administration. The most preferred route is the oral route. The compositions may be conveniently presented in unit dosage forms, and prepared by any methods known in the art of pharmacy.

In the practice of the invention, the most suitable route of administration as well as the magnitude of a therapeutic dose of the compounds according to the invention in any case will depend on the nature and severity of the disease to be treated. The dose, and dose frequency, may also vary according to the age, body weight and response of the individual patient. Special requirements may be needed for patients having Zollinger-Ellison syndrome, such as a need for higher doses than the average patient. Children and patients with liver diseases generally will benefit from doses that are somewhat lower than average. Thus, in some conditions it may be necessary to use doses outside the ranges stated below, for example long-term treatments may request lower dosage. Such higher and lower doses are within the scope of the present invention. Such daily doses may vary between 5 mg to 300 mg.

In general, a suitable oral dosage, form of the compound of the invention may cover a dose range from 5 mg to 300 mg total daily dose, administered in one single dose or equally divided doses. A preferred dosage range is from 10 mg to 80 mg.

The compound of the invention may be combined as the active component in intimate admixture with a pharmaceutical carrier according to conventional techniques, such as the oral formulations described in WO 96/01623 and EP 0 247 983, the disclosures of which are hereby as a whole included by reference.

Combination preparations comprising the compounds of the invention and other active ingredients may also be used. Examples of such active ingredients include, but are not limited to anti-bacterial compounds, non-steroidal anti-inflammatory agents, antacid agents, alginates and prokinetic agents.

The examples below will further illustrate the preparation of the compound of the invention, according to different process routes and including new intermediates. These examples are not intended to limit the scope if the invention as defined hereinabove or as claimed below.

EXAMPLES

Example 1

5-methoxy-2-[[(4-methoxy-3,5-dimethyl-2-pyridinyl)-methyl]sulfinyl]-1H-benzimidazole tert-butyl ammonium salt Omeprazole (1.0 g, 2.9 mmol) was dissolved in tert-butyl methyl ether (10 ml) at 60-70° C. Tert-butylamine (0.60 g, 8.1 mmol) was added and the mixture was then cooled to room temperature whereupon the product crystallised. The formed precipitate was filtered off and washed with in tert-butyl methyl ether. The title compound was obtained as a white solid.

$^1$H-NMR (500 MHz, CDCl$_3$): 1.2 (s, 9H), 2.2, (s, 3H), 2.3, (s, 3H), 3.6 (s, 3H), 3.8 (s, 3H), 4.5 (bs, 3H), 4.7 (m, 2H), 6.9 (m, 1H), 7.0 (d, 1H), 7.5 (d, 1H), 8.2 (s, 1H).

The prepared compound was analysed by XRPD resulting in the diffractogram shown in FIG. 1.

Example 2

S-5-methoxy-2-[[(4-methoxy-3,5-dimethyl-2-pyridinyl)-methyl]sulfinyl]-1H-benzimidazole tert-butyl ammonium salt Esomeprazole sodium salt was dissolved in water and esomeprazole was precipitated by the addition of carbon dioxide.

Esomeprazole (1.0 g, 2.9 mmol) was dissolved in acetonitril (10 ml) at room temperature. Tert-butylamine (0.42 g, 5.7 mmol) was added and the mixture was stirred at room temperature for 2 h. The formed precipitate was filtered off and washed with acetonitril (5 ml). 714 mg (59%) of the title compound was obtained.

Optical rotation $[\alpha]_D^{20}$+26.1 (1% solution in water) $^1$H-NMR (500 MHz, CDCl$_3$): 1.15 (s, 9H), 2.20 (s, 3H), 2.22 (s, 3H), 3.68 (s, 3H), 3.83 (s, 3H), 3.14 (bs, 3H), 4.69-4.80 (m, 2H), 6.90-6.94 (m, 1H), 7.01 (d, 1H), 7.52 (d, 1H), 8.20 (s, 1H).

Figure 2:
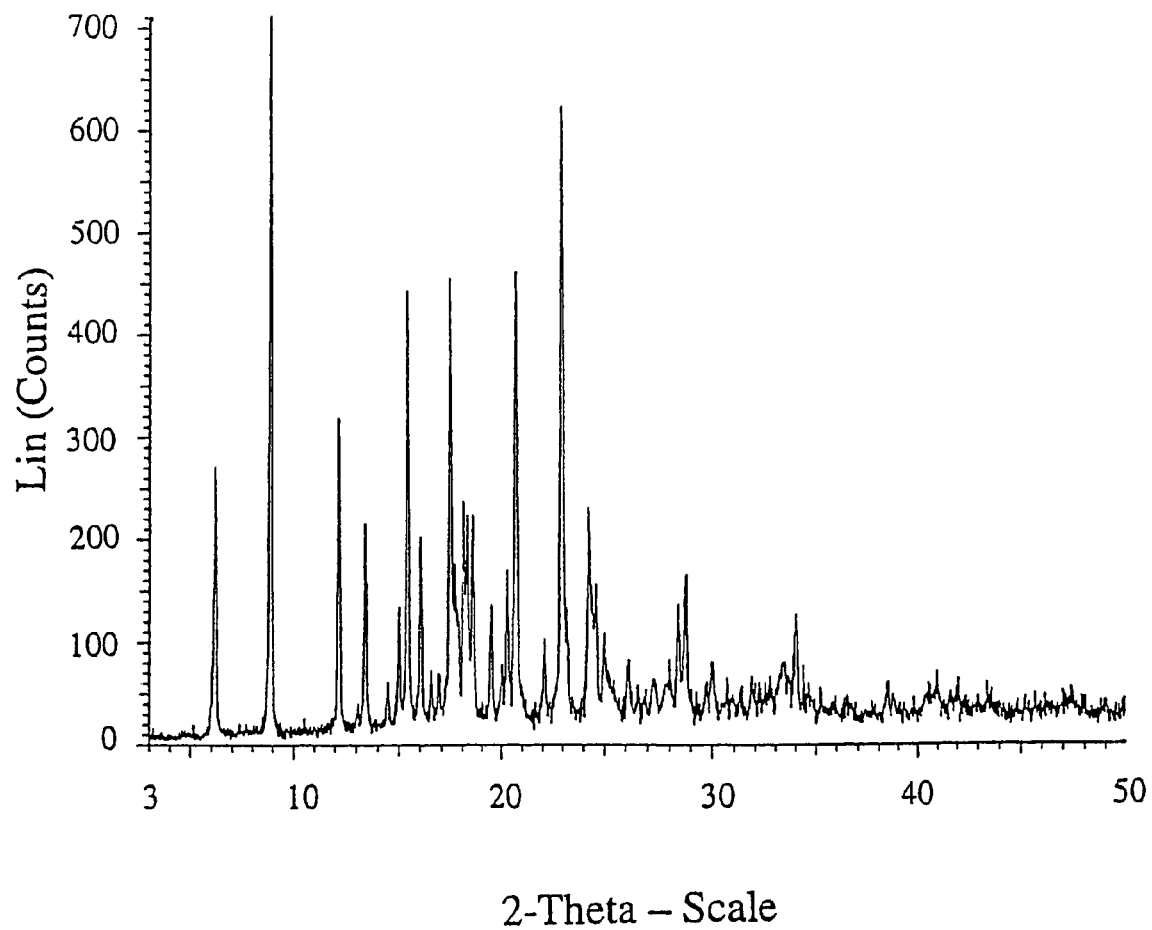
FIG. 2 is an X-ray powder diffractogram of the tert-butylammoniumsalt of esomeprazole.

The prepared compound was analysed by XRPD resulting in the diffractogram shown in FIG. 2.

The invention claimed is:

1. An NHR$_1$R$_2$R$_3^+$ salt of omeprazole, wherein:
   R$_1$ is a linear or branched C$_1$-C$_{12}$-alkyl group, or a cyclic C$_3$-C$_{12}$-alkyl group, wherein the linear or branched C$_1$-C$_{12}$ alkyl group is optionally substituted or interrupted with a substituent selected from the group consisting of a cyclic C$_3$-C$_6$-alkyl group, a cyclic C$_3$-C$_6$-alkylene group, a phenyl group, and a phenylene group, and wherein the cyclic C$_3$-C$_6$-alkyl group, the cyclic C$_3$-C$_6$-alkylene group, the phenyl group, or the phenylene group is optionally further substituted by 0, 1, 2, or 3 methyl groups; and
   R$_2$ and R$_3$ are hydrogen.

2. The NHR$_1$R$_2$R$_3^+$ salt of omeprazole according to claim 1, wherein R$_1$ is a linear or branched C$_1$-C$_6$-alkyl group, or a cyclic C$_3$-C$_6$-alkyl group, wherein the linear or branched C$_1$-C$_6$-alkyl group is optionally substituted or interrupted with a substituent selected from the group consisting of a cyclic C$_3$-C$_5$-alkyl group, a cyclic C$_3$-C$_5$-alkylene group, a phenyl group, or a phenylene group, and wherein the cyclic C$_3$-C$_5$-alkyl group, the cyclic C$_3$-C$_5$-alkylene group, the phenyl group, or the phenylene group is optionally further substituted by 0, 1, 2, or 3 methyl groups.

3. The NHR$_1$R$_2$R$_3^+$ salt of omeprazole according to claim 1, wherein R$_1$ is a linear, branched, or cyclic C$_4$-alkyl group, wherein the linear or branched C$_4$-alkyl group is optionally substituted or interrupted with a cyclic C$_3$-alkyl group or a cyclic C$_3$-alkylene group, and wherein the cyclic C$_3$-alkyl group or the cyclic C$_3$-alkylene group is further substituted by 0, 1, 2, or 3 methyl groups.

4. The NHR$_1$R$_2$R$_3^+$ salt of omeprazole according to claim 1, wherein the salt has a pKa value equal to or greater than about 10.

5. The NHR$_1$R$_2$R$_3^+$ salt of omeprazole according to claim 1, wherein the salt has a pKa value equal to or greater than about 10.5.

6. The NHR$_1$R$_2$R$_3^+$ salt of omeprazole according to claim 1, wherein the salt is the tert-butylammonium salt of omeprazole.

7. The NHR$_1$R$_2$R$_3^+$ salt of omeprazole according to claim 1, wherein the salt is crystalline.

8. A process for preparation of an NHR$_1$R$_2$R$_3^+$ salt of omeprazole according to any one of claims 1-5, 6, or 7 which comprises the steps of:
   a) dissolving omeprazole in an organic solvent;
   b) adding an NR$_1$R$_2$R$_3$ compound and precipitating the desired salt; and
   c) isolating and drying the obtained salt of omeprazole.

9. The process according to claim 8, wherein the organic solvent is acetonitrile or tert-butyl methyl ether.

10. A pharmaceutical composition comprising the NHR$_1$R$_2$R$_3^+$ salt of omeprazole according to any one of claims 1-5, 6, or 7 as active ingredient in association with pharmaceutically acceptable excipients.

11. A method for inhibiting gastric acid secretion comprising administering to a patient suffering from the condition a therapeutically effective amount of the NHR$_1$R$_2$R$_3^+$ salt according to any one of claims 1-5, 6, or 7.

12. An NHR$_1$R$_2$R$_3^+$ salt of esomeprazole, wherein:
   R$_1$ is a linear or branched C$_1$-C$_{12}$-alkyl group, or a cyclic C$_3$-C$_{12}$-alkyl group, wherein the linear or branched C$_1$-C$_{12}$ alkyl group is optionally substituted or interrupted with a substituent selected from the group consisting of a cyclic C$_3$-C$_6$-alkyl group, a cyclic C$_3$-C$_6$-alkylene group, a phenyl group, and a phenylene group, and wherein the cyclic C$_3$-C$_6$-alkyl group, the cyclic C$_3$-C$_6$-alkylene group, the phenyl group, or the phenylene group is optionally further substituted by 0, 1, 2, or 3 methyl groups; and
   R$_2$ and R$_3$ are hydrogen.

13. The NHR$_1$R$_2$R$_3^+$ salt of esomeprazole according to claim 12, wherein R$_1$ is a linear or branched C$_1$-C$_6$-alkyl group or a cyclic C$_3$-C$_6$-alkyl group, wherein the linear or branched C$_1$-C$_6$ alkyl group is optionally substituted or interrupted with a substituent selected from the group consisting of a cyclic C$_3$-C$_5$-alkyl group, a cyclic C$_3$-C$_5$-alkylene group, a phenyl group, or a phenylene group, and wherein the cyclic C$_3$-C$_5$-alkyl group, the cyclic C$_3$-C$_5$-alkylene group, the phenyl group, or the phenylene group is optionally further substituted by 0, 1, 2, or 3 methyl groups.

14. The NHR$_1$R$_2$R$_3^+$ salt of esomeprazole according to claim 12, wherein R$_1$ is a linear, branched, or cyclic C$_4$-alkyl group, wherein the linear or branched C$_4$-alkyl group is optionally substituted or interrupted with a cyclic C$_3$-alkyl group or a cyclic C$_3$-alkylene group, and wherein the cyclic C$_3$-alkyl group or the cyclic C$_3$-alkylene group is further substituted by 0, 1, 2, or 3 methyl groups.

15. The NHR$_1$R$_2$R$_3^+$ salt of esomeprazole according to claim 12, wherein the salt has a pKa value equal to or greater than about 10.

16. The NHR$_1$R$_2$R$_3^+$ salt of esomeprazole according to claim 12, wherein the salt has a pKa value equal to or greater than about 10.5.

17. The NHR$_1$R$_2$R$_3^+$ salt of esomeprazole according to claim 12, wherein the salt is the tert-butylammonium salt of esomeprazole.

18. The NHR$_1$R$_2$R$_3^+$ salt of esomeprazole according to claim 12, wherein the salt is crystalline.

19. A process for preparation of an NHR$_1$R$_2$R$_3^+$ salt of esomeprazole according to any one of claims 12-18, which comprises the steps of:

a) dissolving esomeprazole in an organic solvent;
b) adding an $NR_1R_2R_3$ compound and precipitating the desired salt; and
c) isolating and drying the obtained salt of esomeprazole.

20. The process according to claim 19, wherein the organic solvent is acetonitrile or tert-butyl methyl ether.

21. A pharmaceutical composition comprising the $NHR_1R_2R_3^+$ salt of esomeprazole according to any one of claims 12-18 as active ingredient in association with pharmaceutically acceptable excipients.

22. A method for inhibiting gastric acid secretion comprising administering to a patient suffering from the condition a therapeutically effective amount of the $NHR_1R_2R_3^+$ salt according to any one of claims 12-18.

* * * * *

UNITED STATES PATENT AND TRADEMARK OFFICE
CERTIFICATE OF CORRECTION

PATENT NO. : 7,345,061 B2  Page 1 of 1
APPLICATION NO. : 10/506345
DATED : March 18, 2008
INVENTOR(S) : Mikael Dahlström It is certified that error appears in the above-identified patent and that said Letters Patent is hereby corrected as shown below:

Title Page, Add the following:
Item (60): Related U.S. Application Data:
Provisional application no. 60/362,187, filed on March 5, 2002.

Signed and Sealed this

Tenth Day of March, 2009

JOHN DOLL
*Acting Director of the United States Patent and Trademark Office*